United States Patent
Nagle et al.

(10) Patent No.: US 7,834,255 B2
(45) Date of Patent: Nov. 16, 2010

(54) HYBRID CORN PLANT AND SEED PP88602

(75) Inventors: Barry J. Nagle, Carmel, IN (US); Travis L. Roberts, Brownsburg, IN (US); Brad M. Ostrander, Indianapolis, IN (US); Wade A. Ostrander, Brownsburg, IN (US)

(73) Assignee: Brunob II BV, Arnhem (NL)

( * ) Notice: Subject to any disclaimer, the term of this patent is extended or adjusted under 35 U.S.C. 154(b) by 210 days.

(21) Appl. No.: 12/169,974

(22) Filed: Jul. 9, 2008

(65) Prior Publication Data

US 2010/0009061 A1    Jan. 14, 2010

(51) Int. Cl.
*A01H 5/00* (2006.01)
*A01H 5/10* (2006.01)
*A01H 1/00* (2006.01)
*C12N 5/04* (2006.01)

(52) U.S. Cl. .................... 800/320.1; 800/260; 435/412

(58) Field of Classification Search .................. None
See application file for complete search history.

(56) References Cited

U.S. PATENT DOCUMENTS

| 5,444,177 | A | 8/1995 | Pfund |
| 7,598,436 | B2 | 10/2009 | Nagle |
| 2008/0263709 | A1* | 10/2008 | Bockelman ............ 800/263 |
| 2009/0291190 | A1 | 11/2009 | Nagle et al. |
| 2009/0317534 | A1 | 12/2009 | Nagle et al. |
| 2010/0011459 | A1 | 1/2010 | Ostrander et al. |

FOREIGN PATENT DOCUMENTS

WO    WO 94/03049    2/1994

* cited by examiner

*Primary Examiner*—Anne Kubelik
(74) *Attorney, Agent, or Firm*—Cooley LLP

(57) ABSTRACT

This invention provides hybrid maize plant designated PP88602. This invention further provides hybrid seed of PP88602, hybrid plants produced from such seed, and variants, mutants, and trivial modifications to hybrid PP88602, as well as methods of using the hybrid and products produced from the hybrid.

16 Claims, No Drawings

HYBRID CORN PLANT AND SEED PP88602

FIELD OF THE INVENTION

This invention is in the field of maize breeding, specifically relating to an amylose hybrid maize designated PP88602.

BACKGROUND OF THE INVENTION

All publications and patent applications herein are incorporated by reference for all purposes to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

The goal of plant breeding is to combine in a single variety or hybrid various desirable traits, or to provide a desirable trait without significant detriment to other important properties. For field crops, desirable traits may include resistance to diseases and insects, tolerance to heat, cold and drought, reducing the time to crop maturity, greater yield, and better agronomic quality. With mechanical harvesting of many crops, uniformity of plant characteristics such as germination and stand establishment, growth rate, maturity, and plant and ear height is important. Other desirable traits may be those directly or indirectly associated with special nutritional and industrial types of crops. Examples of such specialty varieties or hybrids include those with higher oil content, different oil profiles, greater protein content, better protein quality or higher amylose content. It is also desirable to produce plants which are particularly adapted to a given agricultural region. New hybrids are an important part of efforts to control raw material costs.

Maize (Zea mays L.) is often referred to as corn in the United States, and the terms are used interchangeably in the present application. Maize has separate male and female flowers on the same plant, located on the tassel and the ear, respectively. Thus, it can be bred by crossing to itself (self-pollination or selfing), to another plant of the same family, line or variety (sib-pollination or sib-crossing) or to another plant of a different family, line or variety (outcrossing or cross-pollination).

Repeated self-pollination of plants, combined with selection for the desired type over many generations, results in inbred lines which are homozygous at almost all loci and thus will produce a uniform population of homozygous offspring when subject to further self-pollination. A cross between two different homozygous lines produces a uniform population of heterozygous hybrid plants. A cross of two plants each heterozygous at a number of gene loci will produce a population of heterogeneous plants that differ genetically and will not be uniform.

Hybrid maize varieties can be produced by a process comprising (1) the selection of plants from various germplasm pools for initial breeding crosses; (2) the selfing of the selected plants from the breeding crosses for several generations to produce a series of inbred lines as described above; and (3) crossing a selected inbred line with a different inbred line to produce the hybrid progeny (F1). Preferably, an inbred line should comprise homozygous alleles at about 95% or more of its loci.

Pedigree breeding and recurrent selection are two examples of methods used to develop an inbred line.

Pedigree breeding starts with the crossing of two or more genotypes, each of which may have one or more desirable characteristics. Superior progeny are selfed and selected in successive generations, during the course of which the level of homozygosity is increased. An inbred line suitable for hybrid production may be produced after a number of generations of selfing and selection, for example after four, five, six or more generations.

Double haploid methods can reduce the number of generations needed to obtain an inbred line. These methods involve the doubling of haploids derived from either the maternal or paternal gametes. Genetics markers can be used to identify haploids, and the haploids doubled to form homozygous diploid lines.

Recurrent selection entails individual plants cross-pollinating with each other to form progeny which are then grown. The superior progeny are then selected by any number of methods, which include individual plant, half sib progeny, full sib progeny, selfed progeny and topcrossing. The selected progeny are cross pollinated with each other to form progeny for another population. This population is planted and again superior plants are selected to cross pollinate with each other. The objective of this repeated process is to improve the traits of a population. The improved population can then be used as a source of breeding material to obtain inbred lines to be used in hybrids.

Backcrossing can be used to improve inbred lines and a hybrid which is made using those inbreds. Backcrossing can be used to transfer a specific desirable trait from one line, the donor parent, to an inbred called the recurrent parent which has overall good agronomic characteristics yet that lacks the desirable trait. This transfer can be achieved by first crossing the recurrent parent with the donor parent, and then performing a backcross in which the progeny are mated to the recurrent parent. The resultant progeny can then be selected for the desired trait, and a further backcross performed using the selected individuals. Typically after four or more backcross generations with selection for the desired trait in each generation, the progeny will contain essentially all genes of the recurrent parent except for the genes controlling the desired trait. The last backcross generation is then selfed to give pure breeding progeny for the gene(s) being transferred.

Other plant breeding techniques known in the art, such as restriction fragment length polymorphism enhanced selection, genetic marker enhanced selection and transformation, may also be used in the production of inbred lines. For example, selection in the breeding process can be based upon the accumulation of markers linked to the positive effecting alleles and/or the elimination of markers linked to the negative effecting alleles from the plant's genome. Often, a combination of techniques is used.

For a review of plant breeding methods well known to those skilled in the art, see, for example, Sprague and Dudley (eds.), Corn and Corn Improvement, Third Edition, American Society of Agronomy, Inc., 986 pages, 1988; Fehr and Hadley (eds.), Hybridization of Crop Plants, American Society of Agronomy, Inc., 765 pages, 1980; Allard, Principles of Plant Breeding, John Wiley & Sons, Inc., 485 pages, 1960; Jensen, Plant Breeding Methodology, John Wiley & Sons, Inc., 676 pages, 1988; Simmonds, Principles of Plant Breeding, Longman Group Limited, 408 pages, 1979; and Hallauer and Miranda, Quantitative Genetics in Maize Breeding, Iowa State University Press, 468 pages, 1981.

In producing a hybrid strain by crossing two different inbred lines, it is advantageous to minimize the possibility of self-pollination. Minimizing self-pollination will minimize the proportion of the resultant seed which is substantially identical to the inbred line (resulting from the self-pollination) and increase the amount of hybrid seed (resulting from cross pollination). To this end, commercial maize hybrid production uses a male sterility system to render the female parent male sterile. There are several ways in which a maize plant can be manipulated so that it is male sterile. These include use of manual or mechanical emasculation (or detasseling), cytoplasmic genetic male sterility, nuclear genetic male sterility or gametocides (chemical agents affecting cells critical to male fertility, for example as described in Carlson, Glenn R., U.S. Pat. No. 4,936,904).

In detasseling, alternate strips of two inbred varieties of maize are planted in a field, and the pollen-bearing tassels are removed from one of the inbreds (female) prior to pollen shed. Providing that there is sufficient isolation from sources of foreign maize pollen, the ears of the detasseled inbred will be fertilized only from the other inbred (male), and the resulting seed is therefore hybrid and will form hybrid plants.

Alternatively, the female line can be cytoplasmic male sterile as a result of an inherited factor in the cytoplasmic genome. This characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. The same hybrid seed, a portion produced from detasseled fertile maize and a portion produced using the CMS system can be blended to insure that adequate pollen loads are available for fertilization when the hybrid plants are grown.

Genetic male sterility may be conferred by one of several available methods, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. A system in which male fertility genes are expressed under an inducible promoter is described in Albertsen et al., U.S. Pat. No. 5,432,068. Other approaches include delivering into the plant a gene encoding a cytotoxic substance associated with a male tissue specific promoter, or an antisense system in which a gene critical to fertility is identified and an antisense to that gene is inserted in the plant (see Fabinjanski, et al. EPO 89/3010153.8 publication no. 329,308 and PCT application PCT/CA90/00037 published as WO 90/08828).

Having obtained a desirable hybrid strain by the crossing of two different parent inbred strains, it is possible to maintain a uniform supply of the hybrid seed. The population of parent plants can be maintained by repeated self pollination. Moreover, since the parents are homozygous, the hybrid produced in the cross will always be the same. Thus, once a desirable hybrid has been identified, a continual supply of hybrid seed having the same properties can be provided.

Objectives of commercial maize hybrid line development include the development of new corn hybrids which are able to produce high yield of grain, which require less investment of time or resources, which are more resistant to environmental stresses (e.g., stresses particular to a certain growing area), which are easier to harvest and/or which provide grain or other products particularly suitable for a desired commercial purpose. To obtain a new hybrid, the corn breeder selects and develops superior inbred parental lines for producing hybrids. This is far from straightforward in view of the number of segregating genes and in view of the fact that the breeder often does not know the desired parental genotype in detail. Then, the breeder must identify the particular cross-combination of inbred lines which produces a desired hybrid. Even having obtained two superior inbred lines, there is no guarantee that the combination of these will produce desirable hybrid F1 plants. This is particularly the case because many selectable traits (e.g., yield) are dependent on the effects of numerous genes interacting with each other. Thus, the selection or combination of two parent lines produces a unique hybrid which differs from that obtained when either of the parents is crossed with a different inbred parent line.

SUMMARY OF THE INVENTION

This invention relates to the development of a new amylose maize hybrid designated as PP88602. PP88602 is higher yielding than currently-grown amylose maize hybrids of similar maturity, type and adaptation. For example, PP88602 yielded 8.5 bushels more per acre than the mean yield a check hybrid when tested together at 4 locations in one year. The yield differential was 6.9 bushels per acre in trials at 4 locations the following year. PP88602 has reduced harvest moisture when compared to other commercial amylose hybrids of similar maturity, improved stalk quality, and is a soft grain type suitable for wet milling. PP88602 further provides corn growers with a new amylose maize hybrid with high agronomic yield that is adapted to the central corn growing belt of the United States.

According to the invention, there is provided a novel corn hybrid, designated PP88602, produced by crossing bC300 and bDL361. These two proprietary inbreds were developed by the pedigree breeding method. Inbreds bC300 and bDL361 are respectively the female and male parents of hybrid PP88602. A representative sample of seed which when grown produces hybrid plants of PP88602 is deposited under American Type Culture Collection ("ATCC") accession number PTA-9638.

In one aspect, the present invention provides hybrid seed, a representative sample of which has been deposited under ATCC accession number PTA-9638. The present invention also provides a population of corn seeds, wherein at least 80%, 81%, 82%, 83%, 84%, 85%, 86%, 87%, 88%, 89%, 90%, 91%, 92%, 93%, 94%, 95%, 96%, 97%, 98%, 99% or 100% of said seeds are hybrid seeds of which a representative sample has been deposited under ATCC accession number PTA-9638.

In another aspect, the present invention relates to a hybrid plant obtainable or obtained by growing seed of which a representative sample is deposited under ATCC accession number PTA-9638.

The invention also relates to variants, mutants and trivial modifications of the hybrid seed or plant.

Seeds, plants, plant parts, somatic tissues or cells according to the present invention may have substantially the same genotype as the deposited seed ATCC PTA-9638, and/or may be capable of serving as the source for tissue culture to produce a plant of substantially the same genotype as hybrid seed deposited under ATCC accession number PTA-9638.

In another aspect the present invention provides a corn plant (or seed thereof) having desirable traits of hybrid PP88602. The corn plant may have all or essentially all of the morphological or physiological characteristics of hybrid PP88602. Optionally, the plant may have one or more additional characteristics, e.g., characteristics resulting from the presence of one or more nucleic acid sequences introduced by techniques known to those skilled in the art, such as transgenic techniques or conventional breeding methods such as backcrossing. In other words, the hybrid corn plants of the present invention include hybrid corn plants of PP88602 which further include one, two, three or more foreign or heterologous genes introduced into PP88602. Such foreign or heterologous genes may be from a different corn plant (i.e., a corn inbred, corn hybrid, corn haploid, etc.) other than the inbreds used to produce PP88602, and/or from a plant species other than *Zea mays* (e.g., alfalfa, soybean, canola, tomato, potato, yew tree, marigold, etc.), and/or from a non-plant species (e.g., bacteria, fungi, insects, mammals, jellyfish, etc.).

The invention further relates to corn plants and seeds derived from hybrid maize PP88602. These plants and seeds may be of an essentially derived variety as defined in section 41(3) of the Plant Variety Protection Act, i.e., a variety that:
  (i) is predominantly derived from hybrid PP88602 or from a variety that is predominantly derived from hybrid PP88602, while retaining the expression of the essential characteristics that result from the genotype or combination of genotypes of hybrid PP88602;
  (ii) is clearly distinguishable from hybrid PP88602; and
  (iii) except for differences that result from the act of derivation, conforms to the initial variety in the expression of the essential characteristics that result from the genotype or combination of genotypes of the initial variety.

An essentially derived variety may be obtained by the selection of a natural or induced mutant or of a somaclonal variant, the selection of a variant individual from plants of hybrid PP88602, backcrossing, transformation by genetic engineering, or any other method.

The essential characteristics may be one or more of the desirable traits set forth herein.

The corn plants and seeds derived from hybrid maize PP88602 may in other embodiments be regenerated from a tissue culture produced from a hybrid PP88602 plant, or may be a plant or seed having hybrid PP88602 as an ancestor, as discussed further below.

The present invention also provides a tissue culture of regeneratable cells produced from hybrid plant PP88602, wherein said tissue culture is capable of producing plants having desirable traits of hybrid PP88602 as set out above. The tissue culture may be derived directly or indirectly from hybrid PP88602. Preferably the tissue culture is capable of producing plants which have all or substantially all of the morphological and physiological characteristics of hybrid PP88602. Optionally, the plants may have one or more additional characteristic, e.g., conferred by a nucleic acid sequence introduced using transgenic or conventional breeding techniques. In some embodiments the plant may have the genetic complement of hybrid PP88602, optionally comprising one or more additional nucleic acid sequences capable of modifying the phenotype of the plant when expressed (e.g., as RNA or protein). The culture can be from any tissue capable of somatic embyrogenesis, e.g., may be selected from the group consisting of leaf, pollen, embryo, root, root tip, anther, silk, flower, kernel, ear, cob, husk, stalk, cell or protoplast.

The invention further relates to the use of the tissue culture to produce a whole plant, to protoplasts produced from said tissue culture and to a corn plant regenerated from said tissue culture. A method of producing a whole plant from the tissue culture may comprise one or more of: culturing cells in vitro in a media comprising an embryogenesis promoting hormone until callus organization is observed; transferring cells to a media which includes a tissue organization promoting hormone; after tissue organization is observed transferring cells into a media without said hormone to produce plantlets; and growing said plantlets, optionally including growing said plantlets on a minimal media for hardening.

In a further aspect of the present invention, there is provided pollen or an ovule of hybrid plant PP88602, as well as seed produced by fertilization with said pollen or of said ovule, and plants grown from the seed.

The hybrid plant PP88602 can be crossed with a corn plant of another line or variety, or can be sib-crossed or selfed to produce another plant, line (e.g., inbred line) or population of plants (e.g., breeding population of plants) which is of benefit in plant breeding.

Thus, in another aspect the present invention relates to a plant or seed produced by a breeding program using hybrid PP88602 as a parent, wherein the plant or seed is a member of a generation of progeny of said parent, e.g., a member of the first, second, third, fourth, fifth, sixth or more generation of progeny. Thus, the present invention includes plants and seeds produced using hybrid PP88602 as an ancestor. Ancestry can be assessed from the records kept routinely by one of ordinary skill in the art. It can also be assessed based on nucleic acid identity, e.g., using molecular markers, electrophoresis and the like. The plant or seed thus produced may have desired characteristics of hybrid PP88602 as discussed above, or may have all of the morphological and physiological traits of hybrid PP88602.

In another aspect the present invention relates to use of a hybrid PP88602 maize plant to produce seed and/or progeny maize plants. The present invention also provides a method comprising providing a plant of hybrid PP88602, crossing it with itself or with another maize plant (which may be another hybrid PP88602 plant or may be a plant of a different line or variety) so as to produce seed, and harvesting said seed. The method may further comprise growing said seed to produce one or more progeny maize plants, and optionally, breeding from one or more of said progeny maize plants to produce progeny seed, which may be harvested. The step of growing the progeny seed and breeding from the resultant maize plants to produce a further population of seed can be repeated over one or more further generations (e.g., in 1, 2, 3, 4, 5, 6 or more further generations). For instance, the progeny may be selfed, sibbed, backcrossed, crossed to a population or the like. By "breeding from" a plant is meant a process of crossing the plant with itself or with another plant of the same or a different variety to produce seed. Selection may be carried out in one or more of the progeny generations. The selection may be for one or more desirable traits of hybrid PP88602, e.g., one or more of amylose content of the starch and agronomic yield. Selection may be done using visual inspection, or using molecular markers.

Plants resulting from such methods would contain desirable traits derived from hybrid PP88602 and thus would benefit from the work of the present inventors and from the disclosure contained herein.

For instance, in one embodiment, a method of the invention may comprise sib or self-pollinating hybrid PP88602 to produce a first generation of progeny plants. The method may further comprise sib or self-crossing said progeny over one or more further generations (e.g., 1, 2, 3, 4, 5, 6 or more further generations) and/or double haploid breeding, in order to produce a plant which is substantially homozygous, e.g., greater than 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.95% or more homozygous. This method may comprise selection of plants having the one or more desirable traits of the parent plant. This selection may take place in each progeny generation or less frequently, e.g., in 1, 2, 3, 4, 5 or more generations of progeny (e.g., in the first progeny generation and/or in one or further progeny generations.

In another embodiment, a hybrid maize plant as described herein can also be crossed to a different variety of maize, such as an inbred line (e.g., an elite inbred line). The F1 progeny generation resulting from this cross would have 50% of its genes derived from the hybrid PP88602. The method may further comprise self-fertilization of one or more plants from the F1 population to produce an F2 progeny generation. Some of the F2 plants will by chance have more than 50% of their genes derived from the parental hybrid plant. These may be selected, for example using molecular marker selection or selection of one or more desired traits of hybrid PP88602. Self-fertilization of the progeny may be carried out over 1, 2, 3, 4, 5 or more further generations to produce an inbred line. Selection may be carried out in each progeny generation, or at a lower frequency, e.g., in 1, 2, 3, 4, 5 or more of the generations.

The method may in some embodiments further comprise modification of the resultant inbred line to provide a further desired trait or traits. For instance, the method may comprise crossing the resultant inbred line with a further plant variety having a desirable trait, and backcrossing the progeny over 1, 2, 3, 4, 5, 6 or more generations so as to insert the desired trait into a genetic background which is substantially that of the inbred line. In another embodiment, the method may comprise transgenic modification of the inbred line, which can be carried out using methods which would be well known to those in the art.

In a further embodiment the method comprises crossing a plant of a first variety or line to a plant of a second, different variety or line, wherein the first variety or line is hybrid PP88602. The second variety or line may be an inbred line and in some embodiments, may be of one of the parental lines of hybrid PP88602. The method may comprise growing a first progeny generation. The method may then further comprise backcrossing one or more plants of that progeny generation to one or more plants of the second variety or line to produce a further progeny generation. The backcrossing may be repeated in 1, 2, 3, 4, 5, 6 or more generations. The last backcross generation may be selfed to result in a pure breeding line for the desired trait(s). Selection may be carried out in one or more of the progeny populations, e.g. to select plants having one or more desirable traits of hybrid PP88602.

The invention also includes the population of seeds or plants produced at any stage of the breeding methods described above. In some embodiments, the seed or plant may be an inbred seed or plant, e.g., such as may be used for a further breeding program or for the development of further hybrids.

Corn is a highly useful crop, and numerous commercial products can be provided by or derived from its different parts. Accordingly, the present invention provides use of a plant as described herein for the production of a processed corn product.

Also provided is a method comprising providing one or more parts of a plant as described herein and processing said part(s) to produce a processed corn product. The method may also comprise growing the plant and/or harvesting said one or more parts.

The plant part may be any of the parts described above, including the stem, husk or cob, but in many embodiments will be the ear or the kernels.

Examples of processed corn products are corn starch (including isolated corn starch components such as amylose or amylopectin), flour, grits, meal, corn syrup or dextrose, corn oil, processed corn grain products such as canned, frozen or pureed grain, ethanol, paper, wall-board or charcoal.

For instance, in one embodiment the invention provides a method for the production of corn starch comprising providing kernels of a plant as described herein, and processing the kernels to produce corn starch. The processing may comprise wet-milling.

In another embodiment, the invention provides a method for the production of corn flour comprising providing kernels of a plant as described herein, and processing the kernels to produce corn flour. The processing may comprise dry-milling.

The invention also provides a method comprising, having provided a processed corn product as described above, using said processed corn product in the production of a manufactured product. These may be any of the manufactured products as described further below. Examples include a food product, packaging, adhesive, paper or textile, pharmaceutical product, cosmetic, and home care product.

The invention further provides a processed corn product or manufactured product produced by any of the methods described above. A preferred processed corn product may be high amylose starch or flour.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, the term "allele" refers to any of several alternative forms of a gene.

As used herein, "starch" refers to starch in its natural or native form as well as also referring to starch modified by physical, chemical, enzymatic and biological processes.

As used herein, "amylose" refers to a starch polymer that is an essentially linear assemblage of D-anhydroglucose units which are linked by alpha 1,6-D-glucosidic bonds.

As used herein, "amylose content" refers to the percentage of the amylose type polymer in relation to other starch polymers such as amylopectin.

As used herein, "area of adaptation" refers to an area having a particular combination of environmental conditions under which this corn hybrid will grow well. The term is not intended to mean that the corn hybrid will not grow outside of this region, particularly, that it will not grow equally well in areas sharing the same or substantially the same combination of conditions.

As used herein, "high amylose maize" or "amylomaize" refer to the generic name for corn that has an amylose content of about 50% or greater. The single recessive amylose-extender gene (ae1), plus modifiers, gives a range in amylose content of about 50% to about 94%. Amylomaize hybrids require special management and cultural requirements to provide more assurance of optimum grain production of acceptable quality and purity. Production fields must be isolated from normal dent corn. High-amylose grain is grown exclusively under contract for wet and dry milling. Amylose starch is utilized in a complexity of uses in various industries. Similar to yield, the actual amylose content of a sample of grain from a particular variety in any particular trial can vary slightly from its overall mean or median amylose content depending on the particular environment in which it is grown. As known by those skilled in the art of growing maize, many factors are involved in determining what constitutes a particular environment for a particular trial/growing season (e.g., rainfall, temperature, soil type, disease incidence, cloud cover, etc.).

As used herein, "amylose maize inbred" refers to maize inbred that has an amylose content of about 50% or greater, wherein the amylose concentration of the grain is determined by the calorimetric method.

As used herein, "amylose maize hybrid" refers to maize hybrid that has an amylose content of about 50% or greater, wherein the amylose concentration of the grain is determined by the colorimetric method.

As used herein, the terms "crossing" or "crossed" or grammatical equivalents thereof refer to pollen from one flower being transfers to the ovule of the same or a different flower to result in fertilization. A plant crossed to itself is self-pollinated or selfed; a plant crossed to another plant of the same variety, family or line is sib-pollinated or sib-crossed and a plant crossed to another plant of a different variety, family or line is out-crossed or out-pollinated.

As used herein, the term "cross pollination" or "crossbreeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the term "elite inbred line" refers to an inbred which has been shown to contribute desirable qualities when used to produce commercial hybrids.

As used herein, the term "female" refers to a plant that produces ovules. Female plants generally produce seeds after fertilization. A plant designated as a "female plant" may contain both male and female sexual organs. Alternatively, the "female plant" may only contain female sexual organs either naturally (e.g., in dioecious species) or due to emasculation (e.g., by detasselling).

As used herein, the term "filial generation" refers to any of the generations of cells, tissues or organisms following a particular parental generation. The generation resulting from a mating of the parents is the first filial generation (designated as "F1" or "$F_1$"), while that resulting from crossing of F1 individuals is the second filial generation (designated as "F2" or "$F_2$").

As used herein, the term "gamete" refers to a reproductive cell whose nucleus (and often cytoplasm) fuses with that of another gamete of similar origin but of opposite sex to form a zygote, which has the potential to develop into a new individual. Gametes are haploid and are differentiated into male and female.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. Thus, this invention further encompasses the maize plants, and parts thereof, of the present invention which have been transformed so that its genetic material contains one or more transgenes operably linked to one or more regulatory elements. Furthermore, the maize plants, or parts thereof, of the present invention also encompass such maize plants, or parts thereof, that contain a single gene conversion.

As used herein, the term "genetic complement" refers to the complete set of alleles possessed by a cell. In a plant or other somatic tissue or cell the complement will be diploid—that is, there will be two alleles (the same or different) at each locus.

As used herein, the term "genotype" refers to the genetic makeup of an individual cell, cell culture, tissue, plant, or group of plants.

As used herein, the term "grain" refers to mature corn kernels produced by commercial growers for purposes other than growing or reproducing the species.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homologue" refers to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "kernel" refers to the corn caryopsis comprising a mature embryo and endosperm which are products of double fertilization.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by the same or different sequences.

As used herein, the term "male" refers to a plant that produces pollen grains. The "male plant" generally refers to the sex that produces gametes for fertilizing ova. A plant designated as a "male plant" may contain both male and female sexual organs. Alternatively, the "male plant" may only contain male sexual organs either naturally (e.g., in dioecious species) or due to removing the ovary.

As used herein, the term "mass selection" refers to a form of selection in which individual plants are selected and the next generation propagated from the aggregate of their seeds.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "ovule" refers to the female gametophyte, whereas the term "pollen" means the male gametophyte.

As used herein, the term "phenotype" refers to the observable characters of an individual cell, cell culture, plant, or group of plants which results from the interaction between that individual's genetic makeup (i.e., genotype) and the environment.

As used herein, the term "recombinant" or "recombinants" refer to a cell, tissue or organism that has undergone transformation with recombinant DNA. The original recombinant is designated as "R0" or "$R_0$." Selfing the $R_0$ produces a first transformed generation designated as "R1" or "$R_1$."

The term "plants" or "plant" or grammatical equivalents thereof as used herein is to be construed broadly to include, as well as whole organisms (i.e., plants, also sometimes called whole plants) at any stage of their development, plant cells, plant protoplasts, tissue culture, plant calli, plant embryos or parts of a plant such as roots, root tips, stalk, leaves, flowers, anthers, ears, cobs, husks, silks, and kernels.

As used herein, the term "seed" refers to mature corn kernels produced for the purpose of propagating the species.

As used herein, the term "self pollinated" or "self-pollination" means the pollen of one flower on one plant is applied (artificially or naturally) to the ovule (stigma) of the same or a different flower on the same plant.

As used herein, "MST PCT" refers to the actual moisture of grain at harvest.

As used herein, "PER CENT DROPPED EARS" refers to the percentage of ears of corn that have detached from the plant and fallen to the ground.

As used herein, "PLTPOP" refers to the percentage of plants which have emerged after planting in comparison to the mean percentage of all hybrids in a common test.

As used herein, "staygreen" refers to a measure of plant health that is determined by the percentage of green tissue compared to desiccated brown tissue on the plant at physiological maturity.

As used herein, "drydown" or "dry down" refer to loss of grain moisture over time.

As used herein, "STKLOD PCT" refers to the percentage of plants in which the stalk is broken below the ear node.

As used herein, "TST/WT LB/BU" refers to a measure of the grain weight in pounds for a given bushel volume.

As used herein, the term "synthetic" refers to a set of progenies derived by intercrossing a specific set of clones or seed-propagated lines. A synthetic may contain mixtures of seed resulting from cross-, self-, and/or sib-fertilization.

As used herein, the term "transformation" refers to the transfer of nucleic acid (i.e., a nucleotide polymer) into a cell.

As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgenic" refers to cells, cell cultures, organisms, plants, and progeny of plants which have received a foreign or modified gene by one of the various methods of transformation, wherein the foreign or modified gene is from the same or different species than the species of the plant, or organism, receiving the foreign or modified gene.

As used herein, the term "variety" refers to a subdivision of a species, consisting of a group of individuals within the species that are distinct in form or function from other similar arrays of individuals.

DETAILED DESCRIPTION OF THE INVENTION

PP88602 is a cross between the female inbred bC300 by the male inbred bDL361. Inbreds bC300 and bDL361 were developed so that each inbred has an amylose starch content between 81% to 85%. Inbreds bC300 and bDL361 were developed using the pedigree method of breeding. Inbred bC300 has a B73/B37 background while bDL361 has a W153R background.

Hybrid PP88602 is characterized by good agronomic yield, average drydown, and good stalk quality. Amylose maize hybrids are generally agronomically inferior to other types of maize hybrids such as dent and waxy grown for commercial production. Hybrid PP88602 has a relative maturity of approximately 115 days based on the comparative relative maturity system for grain harvest moisture. It is adapted to the central corn belt regions of the United States. The hybrid has the following characteristics based on data collected from field plots located in Lebanon, Ind.

TABLE 1

Variety Description Information for PP88602

A. Type: 2 high amylose (1 = Sweet 2 = dent 3 = Flint 4 = Flour 5 = Pop)
Pedigree: bC300 × bDL361
B. Maturity:

| Days | Heat Units | |
|---|---|---|
| 76 | 1560 | From plant emergence to 50% of plants with pollen |
| 78 | 1600 | From Plant emergence to 50% of plants with silk |

TABLE 1-continued

Variety Description Information
for PP88602

C. Plant Characteristics:

| | | Standard Deviation | Sample Size |
|---|---|---|---|
| 224 cm | Plant Height (tassel tip) | 7.23 | 10 |
| 93 cm | Ear Height (base of top ear node) | 4.22 | 10 |
| 0 | Average number of tillers/plant | 0 | 10 |
| 1.2 | Average number of ears/stalk | 0.42 | 10 |
| | Root Color | Munsell code: | 2.5 GY 8/6 |
| 3 | Anthocyanin of brace roots (1 = absent; 2 = faint; 3 = moderate; 4 = dark; 5 = very dark) | | |

D. Leaf

| | | Standard Deviation | Sample Size |
|---|---|---|---|
| 10.5 cm | Width of ear node leaf | 0.85 | 10 |
| 88.5 cm | Length of ear node leaf | 2.42 | 10 |
| | Leaf Color | Munsell code: | 2.5 GY 6/2 |
| open | Leaf Arch | | |

E. Tassel

| | | Standard Deviation | Sample Size |
|---|---|---|---|
| 4.5 | Number of primary lateral branches | 0.97 | 10 |
| 44.3 cm | Tassel length (top leaf collar to tassel tip) | 2.83 | 10 |
| 8 | Pollen shed (1 = light to 9 = heavy) | 0 | 10 |
| | Anther color yellow | Munsell code: | 2.5 Y 7/6 |
| | Glume color | Munsell code: | 10 R 7/8 |
| 10.5 cm | Peduncle length (top leaf to basal branches) | 1.58 | 10 |
| semi-upright | Tassel Arch | | |

F. Ear (unhusked data)

Silk color (3 days after emergence)     Munsell code:     2.5 GY 8/10
    Husk cover (25 days after 50% silking)     Munsell code:     5 GY 7/6
    Dry husk cover (65 days after 50% shedding)     Munsell code:     2.5 Y 8/4
upright    Position of ear at dry husk stage
medium    Husk tightness
2.36 cm    Husk extension (1 = short (exposed); 2 = medium (<8 cm); 3 = long (8-10 cm beyond ear tip); 4 = very long (>10 cm))

G. Ear (husked data)

| | | Standard Deviation | Sample Size |
|---|---|---|---|
| 16.33 cm | Ear length | 3.01 | 10 |
| 4.74 cm | Ear diameter at midpoint | 0.58 | 10 |
| 182.45 gm | Ear weight | 48.15 | 10 |
| 16.2 | Number of kernel rows | 0.63 | 10 |
| 2 | Kernel rows (1 = indistinct; 2 = distinct) | | |
| 1 | Row alignment (1 = straight; 2 = slightly curved; 3 = spiral) | | |
| 2 | Ear taper (1 = slight; 2 = average; 3 = extreme) | | |

H. Kernel (dried)

| | | Standard Deviation | Sample Size |
|---|---|---|---|
| 1.26 cm | Kernel length | 0.09 | 10 |
| 0.71 cm | Kernel width | 0.17 | 10 |
| 0.31 cm | Kernel thickness | 0.03 | 10 |
| 31 | % Round kernels | 4 | 3 |
| | Aleurone color | Munsell code: | 7.5 Y 7/10 |
| | Hard endosperm color | Munsell code: | 2.5 Y 8/10 |
| high amylose | Endosperm type | | |
| 24.98 gm | Weight per 100 kernels | 2.17 | 10 |

I. Cob

| | | Standard Deviation | Sample Size |
|---|---|---|---|
| 2.89 cm | Cob diameter at mid-point | 0.39 | 10 |
| | Cob color Pink | Munsell code: | 10 R 5/6 |

J. Disease resistance (Rate from 1 = most susceptible to 9 = most resistant)

3 Common rust (*Puccinia sorghi*)
    3 Grey leaf spot (*Cercospora zeaemaydis*)
    5 Northern leaf blight (*Exserohilum turcicum*)
    4 Southern leaf blight (*Bipolaris maydis*)
    7 Stewart's wilt (*Erwinia stewarti*)

TABLE 1-continued

Variety Description Information
for PP88602

K. Insect resistance
　　European corn borer (*Ostrinia nubalis*)
　　5 First generation
　　5 Second generation
L. Agronomic traits
　　4 Staygreen (70 days after anthesis, rating scale 1-9, 9 = best)
　　0.1 Per cent dropped ears (70 days after anthesis)

Variants, mutants and trivial modifications of the hybrid seed or plant PP88602 are within the scope of the present invention. A trivial modification may be a modification of the genetic code of the hybrid plant which results in a plant having the desirable traits of hybrid PP88602, as discussed above, and which preferably has all or substantially all of the morphological or physiological characteristics of the hybrid PP88602.

It may be preferred that a seed or plant, e.g., a variant seed or plant, according to the present invention has a genome with at least 90%, 91%, 92%, 93%, 94%, 95%, 96%, 97%, 98%, 99%, 99.5% or 99.9% genetic identity with the genome of hybrid.

A progeny plant of hybrid PP88602 (in any generation) or a plant derived from hybrid PP88602 may preferably have at least 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% or 100% genetic identity with hybrid maize plant PP88602.

The genotype of a plant and the degree of genetic identity to hybrid PP88602 can be assessed using plant breeder records kept routinely by one of ordinary skill in the art. The genotype can additional or alternatively be assessed using molecular marker techniques, e.g, by genetic marker profiling.

A genetic marker profile can be obtained by techniques such as Restriction Fragment Length Polymorphism (RFLP), Randomly Amplified Polymorphic DNA (RAPD), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as microsatellites, and Single Nucleotide Polymorphisms (SNPs). For example see Berry, Don et al "Assessing Probability of Ancestry Using Simple Sequence Repeat Profiles: Applications to Maize Hybrids and Inbreds" Genetics 2002, 161: 813-824.

SSRs are frequently used for mapping purposes. This method is based on repeated sequences which may be repeated a variable number of times at any given locus, thus giving rise to polymorphism, with the potential for multiple alleles. Detection of SSR can be achieved by a number of methods, including PCR. The PCR detection is done using two primers flanking the region containing the repeats (such primers are publicly available). Following amplification, markers can be scored by gel electrophoresis of the amplification products. Scoring of the marker genotype is based on the size of the amplified fragment as measured by molecular weight, rounded to the nearest integer. Relative values should remain constant regardless of the specific primer or precise technique used.

Thus, references to percentage genetic identity may be references to percentage molecular marker profile identity. The molecular marker profile may be an SSR profile. The percentages may refer to the genetic contribution in the molecular marker profile from hybrid PP88602.

It may be preferred that a seed or plant according to the present invention has one or more additional desirable traits and/or one or more inserted nucleic acid sequences conferring a desirable trait when compared to hybrid PP88602. The nucleic acid sequence may be have been inserted into the seed or plant or any progenitor thereof by any of the methods known to one skilled in the art, e.g., by transgenic techniques or by conventional breeding techniques such as backcrossing. Desirable traits include, but are not limited to, insect, pest or disease resistance, resistance to a herbicide, increased drought or cold resistance, male sterility and modification of the properties of the corn grain (e.g., modified fatty acid metabolism, decreased phytate content, modified carbohydrate composition or the like). The source of the nucleic acid may be a plant of the same or different species, or may be any other organism such as an animal (e.g., an insect), prokaryote, fungus, or a virus. The nucleic acid may also be an artificial nucleic acid, i.e., one not appearing in nature.

Specific examples of such genes would be well known to the skilled person, but some which could be used include a *Bacillus thuringiensis* protein, a plant disease resistance gene, a lectin, a vitamin binding protein such as avidin, a protease inhibitor or amylase inhibitor, a mutant EPSP or aroA gene, an antisense ACP gene or a phytase encoding gene. The nucleic acids may be any genetic material capable of modifying the plant's phenotype, e.g., conferring or improving a desirable trait, when expressed in a plant, including antisense nucleic acids, siRNAs and the like as well as nucleic acid sequences encoding proteins. The nucleic acid may also be or comprise an enhancer of a promoter. Examples of suitable nucleic acids can be found in U.S. Pat. No. 6,777, 598, the disclosure of which is incorporated explicitly by reference.

Transgenic methods are well known to those in the art. Both physical and biological methods for plant transformation are well known in the art (see, for example, Miki et al, "Procedures for Introducing Foreign DNA into Plants", in Methods in Plant Molecular Biology and Biotechnology, Glick, B. R. and Thompson, J. E. Eds (CRC Press, Inc, Boca Raton, 1993) pages 67-88). Expression vectors and in vitro culture methods for plant cell and tissue transformation and regeneration of plants are also available. See for example Gruber et al "Vectors for Plant Transformation", in Methods in Plant Molecular Biology and Biotechnology, Glick, B. R. and Thompson, J. E. Eds (CRC Press, Inc, Boca Raton, 1993) pages 89-119, and U.S. Pat. No. 6,118,055.

The present invention also relates in some aspects and embodiments to tissue cultures, to the use of these cultures and to methods comprising producing plants from these cultures.

Duncan, Williams, Zehr, and Widholm, Planta, (1985)165: 322-332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in Plant Cell Reports (1988), 7:262-265 reports several media additions which enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64-65 (1986), refers to somatic embryogenesis from glume callus cultures and B. V. Conger, et al., Plant Cell Reports, 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," Maize for Biological Research (Plant Molecular Biology Association, Charlottesville, Va. 1982, at 367-372) and in Duncan, et al., "The Production of Callus Capable of Plant Regeneration from Immature Embryos of Numerous *Zea Mays* Genotypes," 165 Planta 322-332 (1985).

During the production of hybrid seed, effort is made to prevent self pollination of the inbred parent lines. This can be done by conferring male sterility on one of the parent lines by techniques which will be apparent to the skilled person, including the techniques discussed above. However, in the field, complete male sterility of the female parent is extremely difficult to achieve and so in packaged hybrid seed, there is potential for the inclusion of a small amount of the selfed female parent even when the female seed is or has been treated so as to be male sterile. Also, because the male parent is grown next to the female parent in the field there is the possibility that the male selfed seed could be unintentionally harvested and packaged with the hybrid seed.

Therefore, a population of seeds according to the invention may comprise a majority of seeds produced by hybridization of the two parents, and also comprises levels of seed produced from the selfed parent strains (equivalent to the inbred male and female parent lines) that would be expected to result from the normal methods of producing the hybrid. For example, the seed population may comprise at least 90%, 91%, 92%, 93%, 94%, 95%, 96%, 97%, 98%, 99%, 99.5%, 99.9% or 100% of seed produced from the hybridization of the two parents. The amount of the female inbred line (i.e., seed produced from the selfed female parent) may be less than 10%, 9%, 8%, 7%, 6%, 5%, 4%, 3%, 2%, 1%, 0.5%, 0.4%, 0.3%, 0.2%, 0.1% or 0.05%. The amount of the male inbred line (i.e., seed produced from the selfed male parent) may be less than 5%, 4%, 3%, 2%, 1%, 0.5%, 0.4%, 0.3%, 0.2%, 0.1% or 0.05%.

The self-pollinated plants can be identified and distinguished from the hybrid seed because the self-pollinated plants will be genetically equivalent to one of the inbred lines used to produce the hybrid. Due to the level of homozygosity, they will show decreased vigor when compared to the hybrid. For instance, inbreds are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1-8 (1995), the disclosure of which is expressly incorporated herein by reference. The inbreds can be identified as being homozygous at one or more loci. See also, "Identification of Atypical Plants in Hybrid Maize Seed by Postcontrol and Electrophoresis" Sarca, V. et al., Probleme de Genetica Teoritica si Aplicata Vol. 20 (1) p. 29-42.

INDUSTRIAL APPLICABILITY

Corn has extensive use as animal feed, in providing food for human consumption, and in providing raw materials for industry.

Corn, including both grain and non-grain portions, is extensively used as a feed for livestock, such as pigs, cattle and poultry. The grain is also used for human consumption. In addition, corn kernels can be wet milled to produce corn starch, corn syrup and dextrose, or can be dry milled to produce corn flour, grits and meal. Corn oil is recovered from corn germ, which is a by-product of both the wet and dry milling industries.

Uses of corn starch are based on functional properties such as viscosity, film formation, adhesive properties and the ability to suspend particles. Corn starch can be used in industry in the production of paper, textiles and adhesives. It is also useful in building materials, foundry binders, laundry starches, explosives, oil-well muds, oil-drilling fluids and other mining applications. Due to their biodegradable and renewable nature, starches are increasingly being used many other products, including packaging, plastics, detergents, pharmaceutical tablets, pesticides and cosmetics. Starch can also be fermented into ethanol and can also be processed into corn syrups and sweeteners such as high fructose corn syrup and dextrose. Starch can be used in an unmodified or modified form (e.g., acid modified corn starch, dextrins, oxidized corn starch, pregelatinized starch and chemically derivatized starch).

Corn starch is made up of two components, amylose and amylopectin. Amylose consists of predominantly linear chains of glucose monomers linked by 1,4-glycosidic bonds. In amylopectin, the chains are branched by the addition of 1,6-glycosidic bonds. Starches and flours having different proportions of amylose and amylopectin are particularly adapted to different industrial purposes.

High amylose starch may be recognized by one or more of the following properties. The granules are of two distinct types, spherical and irregular, and are smaller than normal starch granules. The Birefringence End Point Temperature ("BEPT") is reported as 97° C. BEPT is the temperature at which the starch molecule loses organized structure. Some of the granules do not lose all birefringence even after prolonged boiling; swelling power is only about one-fourth and solubles about one-half that of regular corn starch at 95° C. (Corn and Corn Improvement, third edition, Ed. Sprague and Dudley).

High-amylose starches are particularly useful in confectionery such as gummed candies (because they thicken rapidly), in fried snacks (because they resist the penetration of cooking oil), and in photographic film (because of their toughness and transparency), as well as in the uses discussed above (e.g., textiles, biodegradable packaging materials, adhesives for manufacturing corrugated cardboard, and the like). It has also been suggested that the anti-staling properties of bread can be improved by the use of flour high in amylose. Other uses include the sizing of glass fibers prior to weaving, the preparing of a clear, hot water dispersible, edible film for packaging food, dyes and other soluble materials, and coating paper to reduce water and fat absorption.

Nutritional aspects are also important with high amylose starches, particularly high fiber, high resistance to digestion, low calorie, and control of glycemic response.

Amylopectin is particularly useful in paper-making and adhesives (because its branched chains give it greater binding power), and in ready prepared foods, such as in frozen and canned food (because it enhances stability and shelf-life), and fruit pie fillings (where it acts as a thickener). It is useful for the formation of translucent films which are readily redissolved, as well as the uses discussed above.

Other uses of corn include the use of stalks and husks for paper and wall board and the use of cobs for fuel, to make charcoal and for the production of fufural.

EXAMPLES

It should be understood that the examples and embodiments described herein are for illustrative purposes only and that various modifications or changes in light thereof will be suggested to persons skilled in the art and are to be included within the spirit and purview of this application.

Example 1

Hybrid Comparisons for Agronomic Traits

Comparisons of the agronomic characteristics of PP88602 were made to PP88101 which is an amylose hybrid which has similar maturity and adaptation. The comparison is provided in Table 2.

TABLE 2

Hybrid Yield Summary Data for PP88101 and PP88602. Comparison data represent averages of yield trials conducted over a 3 year period at 4 locations in Indiana.

|  | YIELD RU/A 56# | MST PCT | PLTPOP PCT | STKLOD PCT | TSTWT LB/BU |
|---|---|---|---|---|---|
| PP88602 | 110.6 | 14.7 | 98.5 | 14 | 56.86 |
| PP88101 | 103.41 | 15.9 | 99.7 | 7 | 54.51 |
| Reps (#) | 24 | 24 | 24 | 24 | 24 |
| Diff | 7.2 | 1.2 | 1.2 | 7 | 2.4 |

(BU/A #56 = number of bushels per acre of grain yield at 56 lbs per bushel; PCT = percent)

As shown in Table 2, PP88602 has significantly higher agronomic yield than PP88101. PP88602 also shows a significant advantage for stalk quality and has lower moisture at harvest, which possibly will save energy normally used to dry the seed. PP88602 also had test weight advantages over PP88101.

Example 2

Amylose Content

Amylose concentration of the grain was determined by the calorimetric method. Amylose selectively absorbs iodine to produce a highly colored amylose-iodine complex and the intensity of this color is proportional to the amount of amylose present. The percent transmission is determined at 610 nanometers using a spectrophotometer. The percent amylose is obtained from a standard curve. This standard curve is prepared from the percent transmission values obtained with a starch having a known percent amylose content. The calorimetric method used herein is set forth as follows:

Determination of Amylose Content by Colorimetric Analysis
  Equipment:
  1. Tecator Cemotec™ sample mill or equivalent
  2. 4 screw cap glass test tubes with caps, 20×125 mm
  3. 4 screw cap glass test tubes with cap, 20×150 mm
  4. 4 solid PTFE (polytetrafluoroethylene or teflon) stirring rods, 8" in length
  5. Boiling water bath
  6. Centrifuge capable of holding 20×125 mm test tubes
  7. 4 porcelain Büchner funnels, 43 mm plate diameter
  8. Glass microfiber filters, 4.25 cm diameter, 1-1.2 μm porosity (Whatman® #1821-042, VWR #28333-141, or equivalent)
  9. Automated diluter, dual syringe (Hamilton Microlab Series 500® or equivalent)
  10. Glass syringe for diluter, 10 mL
  11. Glass syringe for diluter, 500 μL
  12. Automated flow-injection spectrophotometer, 590 nm wavelength, such as the Foss Tecator FIAStar™ flow-injection analyzer system with Tecator 5042 Detector™, Tecator 5012 Analyzer™, Tecator 5027 Sampler™
  13. Polarimeter, 589 nm wavelength
  14. Vacuum pump
  15. Filter flask, 500 mL
  Reagents:
  Concentrated calcium chloride solution
    3.5 kg of reagent grade calcium chloride dihydrate is dissolved in purified water, cooled to room temperature, and the specific gravity adjusted to 1.3 using calcium chloride or purified water, pH of solution is then carefully adjusted to 2.0 using reagent grade glacial acetic acid, solution is filtered through a medium porosity fritted glass funnel prior to use
  Dilute calcium chloride solution
    600 mL of concentrated calcium chloride solution is made up to 2 L with purified water
  Stock iodine solution
    8.00 g of reagent grade potassium iodide and 4.16 g of reagent grade iodine is dissolved in approximately 10 mL of purified water and made up to 1 L with dilute calcium chloride solution; solution should be stored in an amber bottle
  Working iodine solution
    25 mL of stock iodine solution made up to 200 mL with dilute calcium chloride solution\
  Maize grain sample of known amylose content to serve as the calibration standard
  Procedure:
  1. Finely grind 3-4 g of the calibration standard sample into an appropriate container using the Cemotec™ sample mill.
  2. Repeat step 1 for the experimental sample ensuring the mill is cleaned between the grinding of each sample.
  3. Weigh 0.2 g, 0.4 g, and 0.6 g of the ground calibration standard into three separate 20×125 mm test tubes.
  4. Weigh 0.4 g of the experimental sample into the fourth 20×125 mm test tube.
  5. Add 8 mL of concentrated calcium chloride solution to each of the 20×125 mm test tubes.
  6. Place a PTFE stir rod into each of the 20×125 mm test tubes. Use the rods to disperse the grain.
  7. Place the four 20×125 mm test tubes into the boiling water baths for 30 minutes. Use the stir rods to stir the contents of the test tubes continuously for the first five minutes. Then stir the contents for approximately one minute every five minutes.

8. Remove the test tubes from the water bath. Immediately remove the stir rods without rinsing and allow the samples to cool to room temperature.
9. Add 8 mL of dilute calcium chloride solution to each sample tube. Cap each tube and shake vigorously.
10. Centrifuge the sample tubes at 1,800 RPM for five minutes.
11. Carefully place a 20×150 mm test tube into the filter flask (A sponge can be placed on the bottom of the flask to prevent breakage of the test tube.)
12. Insert the stem of the Büchner funnel into the 20×150 mm test tube. Place a 1-1.2 µM microfiber filter into the Büchner funnel. Turn on the vacuum pump.
13. Decant the solution from one of the 20×125 mm test tubes off of the ground grain that was centrifuged to the bottom and onto the microfiber filter. Allow the sample to filter until all of the solution has passed into the 20×150 mm test tube and the filter is dry.
14. Cap the 20×150 mm test tube and invert a few times to mix sample. The filtered solution should be clear and free of floating particulates at this point. If not, the sample must be re-filtered.
15. Complete steps 11-14 for the experimental sample and for each one of the calibration standard samples.
16. Using an automated dual-syringe diluter, dilute 400 µL of the filtered sample to 10 mL with dilute calcium chloride solution.
17. Analyze the diluted solutions using a flow-injection spectrophotometer. The working iodine solution should be used as the last reagent to be mixed with the injected sample. A flow-injection pump tube with an inner diameter of 0.38 mm can be used to deliver the working iodine where as a flow-injection pump tube with an inner diameter of 0.89 mm can be used to deliver the sample. If necessary, other reagent bottles filled with dilute calcium chloride solution can be used with the flow-injection analyzer to further dilute the sample prior to mixing with working iodine solution. Purified water should be used in the rinse station to rinse the flow cell between analyses.
18. Record the peak absorbance value of the iodine treated solution.
19. Using a remaining portion of the filtered solution from step 14, record the optical rotation of each sample.
20. Using the results from the three calibration standard samples, make a plot of Absorbance vs. (Amylose Content X Optical Rotation.) Determine the slope (m) and y-intercept (b) of this line.
21. Using the values for slope and y-intercept determined in step 20, and the peak absorbance and optical rotation values for the experimental sample, the amylose content of the experimental sample can be determined using the following equation:

$$\% \text{ Amylose} = \frac{\text{peak absorbance} - b}{m \; X \; \text{optical rotation}}$$

The following table provides the percent amylose content of PP88602 compared to PP88101 for three different years at six locations in central Indiana.

TABLE 3

Percent Amylose Content. Comparison data represent averages of trials conducted over a three year period at six locations in Indiana.

| Hybrid | Amylose Content | | | |
| --- | --- | --- | --- | --- |
| | Year 1 | Year 2 | Year 3 | Average |
| PP88602 | 85 | 82 | 84 | 83.6 |
| PP88101 | 83 | 81 | 83 | 82.3 |

As shown in Table 3, PP88602 has higher amylose content than PP88101 but falls within the category of a amylose hybrid based upon the average amylose content of the hybrid over all trials.

Deposit Information

Applicant has made a deposit on Jun. 2, 2008, of at least 2500 seeds for corn hybrid PP88602 (as described herein) under the Budapest Treaty with the American Type Culture Collection (ATCC), P.O. Box 1549, Manassas, Va. 20108 USA, ATCC Accession No. PTA-9638. The seeds deposited with ATCC were taken from the deposit maintained by National Starch and Chemical Company since prior to the filing date of this application. This deposit of the corn hybrid PP88602 will be maintained in the ATCC depository, which is a public depository, for a period of 30 years, or 5 years after the most recent request, or for the enforceable life of the patent, whichever is longer, and will be replaced if it becomes non-viable during that period. Additionally, Applicant has satisfied all of the requirements of 37 C.F.R. §§1.801-1.809, including providing an indication of the viability of the sample, or will do so prior to the issuance of a patent based on this application. Applicant imposes no restriction on the availability of the deposited material from ATCC; however, Applicant has no authority to waive any restrictions imposed by law on the transfer of biological material or its transportation in commerce. Applicant does not waive any infringement of rights granted under this patent.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Although the foregoing invention has been described in some detail by way of illustration and example for the purposes of clarity and understanding, it will be obvious that certain changes and modifications may be practiced within the scope of the invention, as limited only by the scope of the appended claims.

What is claimed:

1. Seed of hybrid maize designated PP88602, a representative sample of which has been deposited under ATCC Accession Number PTA-9638.
2. A maize plant, or part thereof, obtainable by growing the seed of claim 1.
3. A maize plant, or part thereof, wherein the plant, or part thereof, is produced by introducing one or more transgenes operably linked to one or more regulatory elements into the plant, or part thereof of claim 2.
4. A maize plant having all of the morphological and physiological characteristics of the plant of claim 2.

5. A plant part having all of the morphological and physiological characteristics of the plant part of claim 2.

6. A tissue culture of regenerable cells produced from the plant, or part thereof, of claim 2.

7. A maize plant regenerated from a tissue culture of the plant, or part thereof, of claim 2.

8. An ovule of the plant of claim 2.

9. A pollen of a plant of claim 2.

10. A method for producing maize seed comprising crossing the maize plant of claim 2 with itself or another maize plant, and harvesting the resultant seed.

11. The method of claim 10, further comprising growing the resultant seed to produce one or more progeny maize plants, breeding from one or more of said progeny maize plants to produce progeny seed, and harvesting said progeny seed.

12. The method of claim 11, further comprising growing said progeny seed, breeding from the resultant maize plants to produce seed, and harvesting said seed, over 1, 2, 3, 4, 5, 6 or more generations.

13. A seed which when grown produces the plant of claim 4.

14. A method for producing a PP88602-derived maize plant, comprising:
  a) crossing a hybrid maize PP88602 plant with a second maize plant and harvesting the resultant maize seed, wherein representative seed of PP88602 has been deposited under ATCC Accession Number PTA-9638; and,
  b) growing said resultant maize seed to produce a PP88602-derived maize plant.

15. A method for developing a maize plant in a plant breeding program comprising applying plant breeding techniques to a first maize plant, or parts thereof, wherein said first maize plant is the maize plant of claim 4, and wherein application of said techniques results in development of said second maize plant.

16. The method for developing a maize plant in a maize plant breeding program of claim 15 wherein plant breeding techniques are selected from the group consisting of pedigree breeding, recurrent selection, backcrossing, restriction fragment length polymorphism enhanced selection, genetic marker enhanced selection and transformation.

* * * * *